(12) United States Patent
Makarov

(10) Patent No.: US 8,916,362 B2
(45) Date of Patent: Dec. 23, 2014

(54) DEVICES COMPRISING A POLYNUCLEOTIDE TO EXTEND SINGLE STRANDED TARGET MOLECULES

(75) Inventor: Vladimir Makarov, Ann Arbor, MI (US)

(73) Assignee: Swift Biosciences, Inc., Ann Arbor, MI (US)

( * ) Notice: Subject to any disclaimer, the term of this patent is extended or adjusted under 35 U.S.C. 154(b) by 993 days.

(21) Appl. No.: 12/953,071

(22) Filed: Nov. 23, 2010

(65) Prior Publication Data

US 2011/0143401 A1    Jun. 16, 2011

Related U.S. Application Data

(60) Provisional application No. 61/263,700, filed on Nov. 23, 2009.

(51) Int. Cl.
*C12P 19/34* (2006.01)
*C07H 21/04* (2006.01)
*C12Q 1/68* (2006.01)

(52) U.S. Cl.
CPC ............ *C12Q 1/6813* (2013.01); *C12Q 1/6844* (2013.01)
USPC ...................................... 435/91.1; 536/24.33

(58) Field of Classification Search
USPC ...................................... 435/91.1; 536/24.33
See application file for complete search history.

(56) References Cited

U.S. PATENT DOCUMENTS

| | | | | |
|---|---|---|---|---|
| 6,326,145 | B1 * | 12/2001 | Whitcombe et al. | 435/5 |
| 2003/0165917 | A1 | 9/2003 | Ullman et al. | |
| 2009/0011408 | A1 * | 1/2009 | Sorge | 435/6 |

FOREIGN PATENT DOCUMENTS

| | | |
|---|---|---|
| EP | 0971039 | 1/2000 |
| EP | 1923471 | 5/2008 |
| WO | 00/06779 | 2/2000 |
| WO | 2007/146154 | 12/2007 |
| WO | 2009/008854 | 1/2009 |

OTHER PUBLICATIONS

International Search Report and Written Opinion of the International Searching Authority, PCT/US2010/057849, European Patent Office, dated Feb. 22, 2011.

* cited by examiner

*Primary Examiner* — Kenneth Horlick
(74) *Attorney, Agent, or Firm* — Marshall, Gerstein & Borun LLP

(57) ABSTRACT

A polynucleotide device is provided that adds one or more bases to a single stranded polynucleotide. Methods of using the device are provided, comprising contacting a single stranded target molecule with an extension reaction mixture comprising (i) a device or composition of the disclosure, (ii) a polymerase, and (iii) free nucleotides, whereupon an extension reaction product is generated. Kits comprising a device of the disclosure are also provided.

16 Claims, No Drawings

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Synthetic primer

<400> SEQUENCE: 1
ggagagggag aaggg                                          15

<210> SEQ ID NO 2

```
-continued

<211> LENGTH: 84
<212> TYPE: DNA
<213> ORGANISM: Artificial Sequence
<220> FEATURE:
<223> OTHER INFORMATION: Synthetic nucleotide

<400> SEQUENCE: 2
aaaggagagg gagaagggct ccgtaccggc cgcttttttg cggccggtac ggagcccttc    60
tccctctccc ccttctccct ctcc                                          84

<210> SEQ ID NO 3
<211> LENGTH: 132
<212> TYPE: DNA
<213> ORGANISM: Artificial Sequence
<220> FEATURE:
<223> OTHER INFORMATION: Synthetic nucleotide

<400> SEQUENCE: 3
aaaaaagagg agaggggaaa ggagagggga gagggagaag ggctccgtac cggccgcttt    60
tttgcggccg gtacggagcc cttctccctc tccctctcc tttccctct cctctttccc    120 ttctccctct cc                                                       132
```

DEVICES COMPRISING A POLYNUCLEOTIDE TO EXTEND SINGLE STRANDED TARGET MOLECULES

CROSS-REFERENCE TO RELATED APPLICATIONS

This application claims the priority benefit under 35 U.S.C. §119(e) of U.S. Provisional Patent Application No. 61/263,700, filed Nov. 23, 2009, the disclosure of which is incorporated herein by reference in its entirety.

BACKGROUND

DNA replication plays a central role in life. Using specialized enzyme—DNA polymerases, and some auxiliary proteins, cells and viruses are able to precisely copy the genetic information of the primary organism to create its multiple copies.

Polynucleotide replication plays a crucial role in many in vitro nucleic acid diagnostic and research tools. For many years polynucleotide replication has been used as a key reaction in polynucleotide sequence analysis that include a traditional gel-based sequence analysis (Sanger method) and a more recent highly parallel polynucleotide sequencing technology (for example, Solexa platform).

Polynucleotide replication is also a part of several current methods of genotyping. It is routinely used for labeling a polynucleotide with fluorescent dyes for microarray analysis, and it is used for in situ detection using Primed In Situ Labeling (PRINS).

However, one of the most important applications of polynucleotide replication is amplification. Examples include but not limited to Polymerase Chain Reaction (PCR), Strand Displacement Amplification (SDA), Rolling Circle Amplification (RCA), Helicase-Dependent Amplification (HDA), Single Primer Isothermal Amplification (SPIA), etc.

Many of polynucleotide amplification methods rely on the primer extension reaction repeated multiple times. To achieve this goal it is important to dissociate the polynucleotide polymerization product from its nucleic acid template. In PCR such dissociation is achieved by heating the duplex polynucleotide product repeatedly up to 95° C. In other methods, such as SDA, HDA and SPIA, dissociation of the extended product is facilitated by additional enzymes such as restriction endonuclease or nickase (SDA), RNase H (SPIA), or helicase (HDA).

Rolling circle amplification (RCA) is a unique example of primer extension reaction where multiple rounds of replication of a circular polynucleotide template can be achieved without thermal denaturation of double stranded polynucleotides or additional enzymes. The product of RCA is a repetitive sequence $(cA)_n$ where A is a sequence of the circular template and cA is its complement. However, this technique is limited to the synthesis of only this type of extension product. RCA cannot be used to synthesize, for example, more complex sequence combinations like cABC or $(cABC)_n$, wherein each of A, B, and C is a unique sequence and cABC is the complement of ABC. While this limitation of RCA to synthesize molecules like $(cABC)_n$ is likely due to the fact that the production of the circular polynucleotide templates used in this technique requires special circularization and purification procedures, which consequently limits the size of the template, and, in turn, limits the size of the extension product, the limitation to synthesize a non-repetitive sequence like cABC comes from difficulty to control circular DNA replication. Another drawback of RCA is that only some of the target polynucleotides are elongated, while others are left unreacted (and non-extended).

In view of the foregoing, there exists a need in the art for efficient methods of primer extension where (i) multiple rounds of replication of a polynucleotide template are achieved without thermal denaturation of double stranded polynucleotides and without the use of additional enzymes for dissociation of the template from the extension product, (ii) the type (e.g., complexity, size) of the extension products synthesized are not restricted by complicated template production procedures, and (iii) each of the intended target molecules are elongated in an evenly distributed fashion.

SUMMARY OF THE INVENTION

A device for extension of a single stranded target molecule is provided. In some embodiments, the device is a polynucleotide comprising Structure 1:

Structure 1

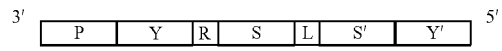

wherein:
P is a primer sequence;
Y is product sequence;
R is replication blocking group;
S is a stem sequence;
L is a loop region;
S' is a sequence which hybridizes to S;
Y' is a sequence which hybridizes to Y; and
wherein each of S and S' is optionally present in the device, wherein the presence of S' is dependent on the presence of S, wherein Y, R, S, L, S', and Y' form a hairpin structure.

In other embodiments, the device for extension of a single stranded target molecule comprises a first polynucleotide of Structure 2:

Structure 2

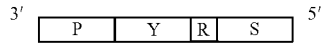

and a second polynucleotide of Structure 3:

Structure 3

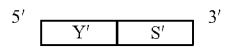

wherein:
P is a primer sequence;
Y is product sequence;
R is replication blocking group;
S is a stem sequence;
Y' is a sequence which hybridizes to Y;
S' is a sequence which hybridizes to S;
and wherein Y and Y' and S and S' form a duplex structure.

In one aspect of the device, sequence S and sequence S' form a duplex structure which is stable at a temperature between about 0° C. and about 95° C., e.g., about 20° C. and about 95° C., about 37° C. and about 95° C., between about 60° C. and about 70° C. or between about 60° C. and about 75° C.

In another aspect of the device, sequence P is about 6 bases to about 30 bases in length.

In another aspect of the device, sequence Y consists of a sequence $P_Y$ which is identical to priming sequence P. In an alternative aspect of the device, sequence Y comprises a sequence $P_Y$ which is identical to priming sequence P.

In yet another aspect of the device, sequence Y further comprises a tag sequence T which is different from the sequence $P_Y$ and tag sequence T is located 3' to sequence $P_Y$ and 5' to primer sequence P.

In another aspect of the device, sequence T is about 15 bases to about 50 bases in length.

In still another aspect of the device, sequence Y consists of an additional sequence A which is not identical to priming sequence P. In one embodiment, sequence A is about 15 bases to about 50 bases in length.

In another aspect, the device comprises a 3' blocking group F which blocks extension of a sequence of the device, wherein blocking group F is located 3' to sequence P in the device. In various embodiments, blocking group F is an amino group, a phosphate, or a dideoxynucleotide.

In still another aspect, the device comprises one or more non-cleavable bonds, e.g., modified internucleotide linkages which are not cleavable by an enzyme. In another aspect, the device comprises a sequence X located 5' to sequence Y' and sequence X comprises a nucleotide sequence of about 1 base to about 25 bases in length, wherein sequence X (i) does not hybridize to sequence P, (ii) hybridizes to at least a portion of sequence P, or (iii) hybridizes to at least a portion of sequence P and to at least a portion of sequence Y. In various embodiments, X hybridizes to only a portion of P or hybridizes to only a portion of P and to only a portion of Y. In other aspects, X does not hybridize to P and X comprises a nucleotide sequence of about 1 to about 10 bases in length.

In another aspect of the device, R is (i) an abasic site, (ii) a modified base, (iii) a base which is absent from product sequence Y or is present in a reaction mixture at a limiting concentration, or (iv) a spacer. In one embodiment, the modified base comprises a chemical moiety which sterically hinders a polymerase activity to or beyond R. In another embodiment, the modified base is a base which is cross-linked to another base of the oligonucleotide. In still another embodiment, the modified base is cross-linked to a base of S'. In yet another embodiment, the abasic site does not specifically bind to a base of sequence S' or sequence Y'. In other embodiments, the spacer is a hexamethylene glycol spacer, a hexylene glycol spacer, or a 2-deoxyribose spacer.

In another aspect of the device sequence S comprises a GC content between about 70% and about 100% or about 0% to about 100%.

Also provided is a composition comprising a device having two polynucleotides (e.g., a first polynucleotide of Structure 2 and a second polynucleotide of Structure 3, as described herein), wherein the second polynucleotide is present at a concentration greater than the concentration of the first polynucleotide. In another aspect of the composition, the concentration of the second polynucleotide is at least 2× greater than the concentration of the first polynucleotide.

In another embodiment, a composition is provided comprising at least two devices as disclosed herein. In one aspect, at least two devices in the composition comprise a first device comprising a product sequence $Y_1$ and a second device comprising a product sequence $Y_2$, wherein $Y_1$ is different from $Y_2$. In another aspect, the composition comprises a plurality of devices as described herein, wherein the plurality comprises at least three subsets of devices, wherein each device of a subset comprises a product sequence Y which is (i) the same as the sequence Y of another device of the same subset and (ii) different from the sequence Y of a device of another subset of the plurality.

A kit is also provided comprising a device as described herein and/or a composition as described herein and instructions for using the device or composition in a reaction which extends a single stranded primer. In one aspect, the kit comprises the single stranded target molecule. In another aspect, the kit comprises a polymerase and free nucleotides. In some aspects, the kit comprises a strand displacement polymerase, e.g., a polymerase with strand displacement activity. In other aspects, the kit comprises a DNA polymerase or an RNA polymerase, or a combination thereof. In specific aspects, the kit comprises a 5' exonucleaseminus polymerase.

In specific aspects, the kit comprises a polymerase that dissociates from the device when in contact with replication blocking group R. In particular aspects, the kit comprises a polymerase that dissociates from the device under isothermal conditions. In yet other aspects, the kit comprises a chaperone strand displacement molecule, e.g., a helicase, a transferase, a single-stranded binding protein.

In further aspects, the kit comprises at least two polymerases, wherein at least one polymerase is a proofreading polymerase. When present, the proofreading polymerase removes bases from the single stranded target molecule that are added via one or more non-template addition reactions.

In another aspect, the kit comprises a molecular beacon comprising a detectable label and a sequence which hybridizes to an extension product of an extension reaction. In still another aspect of the kit, the molecular beacon forms a hairpin structure when not hybridized to the product.

In other aspects, the kit comprises a probe comprising a sequence which hybridizes to an extension product of an extension reaction, wherein the probe optionally comprises a detectable label. In yet another aspect, the kit comprises an enzyme which cleaves an extension product.

In another embodiment, a method of extending a single stranded target molecule is provided, the method comprising contacting the single stranded target molecule with an extension reaction mixture comprising (i) a device as provided herein and/or a composition as provided herein, (ii) a polymerase, and (iii) free nucleotides, whereupon an extension reaction product is generated, wherein an extension product of the reaction comprises the single stranded target molecule with a 3' sequence complementary to product sequence Y of the device.

In one aspect of the method, the extension reaction mixture comprises a device wherein product sequence Y consists of a sequence A of about 20 bases to about 30 bases in length, and the extension product includes a 3' terminal sequence complementary to sequence A.

In another aspect of the method, the extension reaction mixture comprises a device wherein product sequence Y of the oligonucleotide consists of a sequence $P_Y$ which is identical to primer sequence P of the device, whereupon the target molecule sequence is complementary to the primer sequence P and the reaction product has a 3' terminal sequence that is complementary to the primer sequence P.

In another aspect of the methods, the extension reaction mixture comprises a device wherein product sequence Y of the device comprises sequence $P_Y$ which is identical to primer sequence P of the device and further comprises a tag sequence T which is different from the sequence of sequence $P_Y$ and sequence T is located 3' to $P_Y$.

In another aspect of the method, the extension reaction mixture comprises a plurality of devices of as described herein, wherein the plurality comprises at least three subsets of devices, wherein each device of a subset comprises a sequence Y sequence which is (i) the same as sequence Y of another device of the same subset and (ii) different from sequence Y of a device of another subset of the plurality, wherein the extension product has a 3' terminus which comprises a sequence which is complementary to each of sequence Y of the plurality.

In other aspects, the method is carried out under substantially isothermal conditions. In specific aspects, the method is carried out at a temperature within a range of about 60° C. to about 75° C. In alternative aspects, the method comprises one or more steps carried out at a first temperature and one or more steps carried out at a second temperature, wherein the second temperature is at least or about 25° C. greater than the first temperature. In certain aspects, the first temperature is within a range of about 60° C. to about 75° C. and the second temperature is within a range of about 85° C. to about 100° C. In particular aspects, the method comprises a dissociation step in which the polymerase dissociates from the device at the second temperature.

DESCRIPTION OF THE INVENTION

Provided herein is a polynucleotide device that catalyzes the addition of one or more polynucleotide sequences to the 3' end of a single-stranded polynucleotide molecule in the presence of a polymerase. Methods utilizing the device are also provided. A major difference between standard primer-extension reaction and the reaction catalyzed by a device of the invention is that in the first case the reaction is terminated upon completing replication of the template, while in the second case multiple reactions can occur in a coordinated fashion in a single step and result in the programmed synthesis of a long polynucleotide molecule.

Without being bound by a specific mechanism, the device provided herein functions by first hybridizing to a target sequence at a single stranded region of the device. This single stranded region, the primer sequence P, is adjacent to a double stranded region formed by hybridization between product sequence Y, positioned 5' to primer sequence P, and sequence Y' which is all or in part complementary to product sequence Y, and, optionally, by hybridization between stem sequence S, positioned 5' to Y (and R) and sequence S', which is all or in part complementary to stem sequence S. In the presence of a polymerase and under appropriate conditions, the target sequence is extended to add a sequence complementary to product sequence Y, with product sequence Y serving as a template for polymerase activity. As the target sequence is extended, it displaces sequence Y' in the duplex region of the device. Extension of the target sequence continues until a replication blocking group R is reached. When extension of the target sequence is complete, strand migration of sequence Y' displaces the extended target sequence (now in duplex form with product sequence Y) and the double stranded duplex between sequence Y and sequence Y' is restored. The extended target sequence is then dissociated from the device. This process is in one aspect repeated with the same or a different device as long as the product of the extension process terminates with a sequence that can hybridize to the primer sequence P of the same device or a different device.

In certain aspects, the device is a single polynucleotide or a combination of two or more polynucleotides.

In one aspect, the device is synthesized using standard oligonucleotide synthesis techniques. The device is useful in various aspects to add specific polynucleotide sequences to a single stranded molecule such as, for example and without limitation, ABCDEF wherein each of A, B, C, D, E and F are unique polynucleotide sequences. Alternatively, the device provided is useful in other aspects to create repetitive sequences such as XXXXXX wherein X is a specific polynucleotide sequence at the terminus of a target molecule. In still another aspect, the device is used to add polynucleotide sequences combinations such as (ABCDEF)$_n$ to a target molecule. In yet another aspect, the device and methods of its use provided extend evenly all polynucleotide termini in a population of target molecules.

I. General Structure

Accordingly, a device is provided that allows for extension of a single stranded primer, e.g., a single stranded target molecule. In a first embodiment, the device comprises Structure 1:

Structure 1 wherein:
P is a priming sequence;
Y is product sequence;
R is replication blocking group;
S is a universal stem sequence;
L is a loop region;
S' is a sequence which hybridizes to S;
Y' is a sequence which hybridizes to Y; and
wherein each of S and S' is optionally present in the device, wherein the presence of S' is dependent on the presence of S in the device,
wherein Y, R, S, L, S', and Y' form a hairpin structure.

In this single polynucleotide device, the hairpin secondary structure is stable under conditions that allow the target to hybridize to the primer sequence P. In certain embodiments, the hairpin structure is stably maintained throughout the target extension process.

In another embodiment, a polynucleotide pair is provided for extension of a single stranded primer, wherein the polynucleotide pair comprises a first polynucleotide of Structure 2:

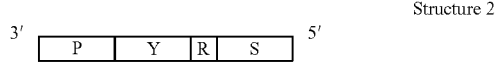

Structure 2 and a second polynucleotide of Structure 3:

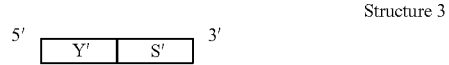

Structure 3 wherein:
P is a priming sequence;
Y is product sequence;
R is replication blocking group;
S is a universal stem sequence;
Y' is a sequence which hybridizes to Y;
S' is a sequence which hybridizes to S.
and wherein Y and Y' and S and S' form a duplex structure.

In this embodiment of the device comprising more than one polynucleotide, the duplex structure formed between sequence Y and sequence Y' is stable under conditions that allow the target to hybridize to the primer sequence P. In one aspect, the polynucleotides of the device maintain at least a degree of association by interaction between sequence S and sequence S'. In one aspect, the polynucleotides of the device remain completely associated throughout the extension process, however, in other aspects, the polynucleotides of the device are at certain instances completely dissociated. Re-association of the polynucleotides of the device is enhanced in certain aspects, by controlling reaction conditions, and/or by providing a molar excess of the polynucleotide having Structure 3 relative to the concentration of the polynucleotide of Structure 2.

II. Structural Features

A. Primer Sequence P

As discussed above, the primer sequence P is the sequence in the device through which at least the 3' end of the target molecule hybridizes to the device. In one aspect, the 3' end of the target molecule and primer sequence P are 100% complementary. In another aspect, the 3' end of the target molecule and primer sequence P are less than 100% complementary but still sufficiently complementary so that the two sequences will stably hybridize under appropriate conditions to allow polymerase extension of the target molecule. In yet other aspects, the target molecule in its entirety is 100% complementary to primer sequence P. In alternative aspects, the target molecule in its entirety is less than 100% complementary but still sufficiently complementary so that the target molecule in its entirety stably hybridizes under appropriate conditions to primer sequence P.

In various aspects, priming sequence P is from X bases to Y bases in length, wherein X is 1, 2, 3, 4, 5, 6, 7, 8, 9, 10, 11, 12, 13, 14, or 15 and Y is about 20, about 25, about 30, about 35 about 40, about 45, about 50, about 55, about 60, about 65, about 70, about 75, about 80, about 85 about 90, about 95 or about 100. In one aspect, priming sequence P in the device is about 5 bases to about 15 bases in length or alternatively, priming sequence P in the device is about 5 bases to about 30, about 5 bases to about 45 bases or about 5 bases to about 60 bases in length. In various other embodiments, priming sequence P is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

B. Product Sequence Y

Product sequence Y is a polymerase template in the device; the complement of product sequence Y is the sequence that is added to the extended target molecule.

Product sequence Y, in certain aspects, is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 30, about 35 about 40, about 45, about 50, about 55, about 60, about 65, about 70, about 75, about 80, about 85 about 90, about 95 or about 100. In other aspects, product sequence Y is about 10 bases to about 75 bases in length. Alternatively, sequence Y is about 10 bases to about 70 bases, about 10 bases to about 65 bases, about 10 bases to about 60 bases, about 10 bases to 55 bases, about 10 bases to about 50 bases in length, about 10 bases to about 45 bases in length, about 10 bases to about 40 bases in length, about 10 bases to about 35 bases in length, about 10 bases to about 30 bases in length, about 10 bases to about 25 bases in length, about 10 bases to about 20 bases in length or about 10 bases to about 15 bases in length. In various other embodiments, the product sequence Y is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

1. Sequence $P_Y$

In certain aspects, the product sequence Y consists of a sequence $P_Y$ which is identical to priming sequence P. Alternatively, product sequence Y comprises a sequence $P_Y$ which is identical to priming sequence P. In embodiments wherein the product sequence Y is $P_Y$, extension of the target molecule results in the complement of the primer sequence P being added to the target molecule. Because the resulting extension product terminates at its 3' end with a sequence that is complementary to the priming sequence P (cP), the target molecule can be extended multiple times in the same reaction mixture, each extension reaction adding a sequence to the target that is complementary to the primer sequence P (cP). Accordingly, in some embodiments, the extension product synthesized comprises a structure 5'-cP-$(P_Y)_n$-3', which is identical to 5'-$(cP)_m$-3', wherein n+1=m.

In various aspects, sequence $P_Y$ is from X bases to Y bases in length, wherein X is 1, 2, 3, 4, 5, 6, 7, 8, 9, 10, 11, 12, 13, 14, or 15 and Y is about 20, about 25, about 30, about 35 40, about 45, about 50, about 55, about 60, about 65, about 70, about 75, about 80, about 85 about 90, about 95 or about 100. In one aspect, sequence $P_Y$ in the device is about 5 bases to about 15 bases in length or alternatively, sequence $P_Y$ in the device is about 5 bases to about 30, about 5 bases to about 45 bases or about 5 bases to about 60 bases in length. In various other embodiments, sequence $P_Y$ is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

2. Tag Sequence T

In certain aspects, product sequence Y comprises a sequence $P_Y$ and tag sequence T which is different from the sequence of $P_Y$. As above, $P_Y$ is identical to primer sequence P. Tag sequence T is located 3' to $P_Y$ and 5' to P (3'-P-T-$P_Y$-5'). In embodiments wherein product sequence Y is 3'-T-$P_Y$-5', the target sequence is extended from the complement of primer sequence P (cP), which hybridizes to primer sequence P, to include the complement of tag sequence T (cT), and the complement of sequence $P_Y$ (c$P_Y$) which is the same as the complement of primer sequence P. As in reactions where product sequence Y is $P_Y$, the extension product of this reaction has a 3' sequence 5'-cP-cT-c$P_Y$-3' and since the c$P_Y$ sequence portion of the extension product is complementary to primer sequence P, the extended target sequence can be further extended multiple times in the same reaction mixture to add multiple copies of 5-'cT-c$P_Y$-3' to the target molecule. In exemplary aspects, the primer sequence P of the device binds to c$P_Y$ of the extension product synthesized in the first round, and, upon a second round of extension, the extension product comprises a sequence of 5' cP-(cT-c$P_Y$)$_2$-3'. The primer sequence P of the device binds to c$P_Y$ of the extension product synthesized in the second round, and upon a third round of extension, the extension product comprises a sequence of 5'-cP-(cT-c$P_Y$)$_3$-3'. Accordingly, in some embodiments, the extension product synthesized comprises a structure 5'-cP-(cT-c$P_Y$)$_n$-3'.

The tag sequence T is, in various embodiments, from X bases to Y bases in length, wherein X is 1, 2, 3, 4, 5, 6, 7, 8, 9, 10, 11, 12, 13, 14, or 15 and Y is about 20, about 25, about 30, about 35 about 40, about 45, about 50, about 55, about 60, about 65, about 70, about 75, about 80, about 85 about 90, about 95 or about 100. In other aspects, tag sequence T is about 10 bases to about 75 bases in length, about 10 bases to about 70 bases, about 10 bases to about 65 bases, about 10 bases to about 60 bases, about 10 bases to 55 bases, or about 10 bases to about 50 bases in length, about 10 bases to about 45 bases in length, about 10 bases to about 40 bases in length, about 10 bases to about 35 bases in length, about 10 bases to about 30 bases in length, about 10 bases to about 25 bases in length, about 10 bases to about 20 bases in length or about 10 bases to about 15 bases in length. In other embodiments, tag sequence T is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

3. Additional Sequence A

In another embodiment of the device, product sequence Y comprises an additional sequence A which is not identical to priming sequence P. In some embodiments, Y consists of additional sequence A. The extended target molecule has a 3' terminal sequence that is complementary to sequence A. In this embodiment, only a single copy of the sequence cA is added to the target molecule in a single reaction mixture in the absence of another device in the same reaction mixture which has a primer sequence P that is identical to additional sequence A. Accordingly, in some embodiments, the extension product synthesized comprises a structure 5'-cP-cA-3'.

In certain aspects, the additional sequence A is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 20, about 25, about 30, about 35 about 40, about 45, about 50, about 55, about 60, about 65, about 70, about 75, about 80, about 85 about 90, about 95 or about 100. In other aspects, additional sequence A is about 20 bases to about 30 bases in length. In other embodiments, the added sequence A is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

C. Internal Blocking Group R

The device further includes an internal replication blocking group R which, in various embodiments and without limitation, is or comprises an abasic site, a modified base, or a base (or bases) that is (are) absent from product sequence Y, or the corresponding complementary deoxynucleotide triphosphate R' is present in a reaction mixture at a limiting concentration or is absent from the reaction mixture.

As used herein, the term "abasic site" refers to a molecule comprising a unit compound that is structurally similar to a nucleotide in that the compound comprises a pentose group bound to one or more phosphates, but differs from a nucleotide in that it lacks a base (e.g., adenine, guanine, cytosine, uracil, thymine, and the like). In some aspects, an abasic site is a ribose or deoxyribose bound to one to three phosphate groups. In some aspects, the abasic site is a molecule comprising more than one unit compounds, as described above, connected together in the same manner as a polynucleotide. When in contact with an abasic site, a polymerase does not add a nucleotide to the single stranded target molecule, since there is no base template at this site.

In aspects wherein the blocking group R is a modified base, the modified base comprises, in one aspect, a chemical moiety which sterically hinders binding of a polymerase to blocking group R. In exemplary aspects, R is a biotinylated base complexed with a streptavidin molecule.

Alternatively, the modified base is a base which is cross-linked to another base of the device, and in certain aspects, the modified base is cross-linked to a base of S', or any other base which is located 3' to Y' and 5' to Y. In specific aspects, the modified base forms a Psoralen interstrand crosslink with another base of the device, e.g., a base of S' or any other base which is located 3' to Y' and 5' to Y. In aspects, wherein blocking group R is an abasic site, this abasic site does not specifically bind to a base of S' or Y'.

The worker of ordinary skill in the art will appreciate that any replication blocking group is contemplated for use as an R group as long as the blocking group is capable of being incorporated into the structure of the device. In exemplary aspects, the R group is any replication blocking group that does not hinder the device from forming a hairpin structure or duplex structure, when the device is unbound to a polymerase or single stranded target molecule. In some aspects, the R group is any replication blocking group that causes a polymerase to dissociate from the device, e.g., under substantially isothermal conditions, at temperatures within a range of about 0° C. to about 95° C., about 20° C. to about 95° C., about 37° C. to about 95° C., about 60° C. to about 75° C.

In view of the foregoing, the internal replication blocking group R, in some embodiments, is a spacer, such as a bifunctional spacer (e.g., a bifunctional spacer comprising an α,ω-diol). In some aspects, the internal replication blocking group comprises the structure HO-k-OH, wherein k represent a straight or branched alkylene chain, a straight or branched alkenylene chain, or a straight or branched alkynylene chain, wherein k comprises 1 to 10 carbon atoms, e.g., 1, 2, 3, 4, 5, 6, 7, 8, 9, 10 carbon atoms. In some aspects, the internal replication blocking group R is a C1-C10 alkylene glycol spacer, a deoxyribose spacer. In specific aspects, internal replication blocking group R is a hexamethylene glycol spacer, a hexylene glycol spacer, or a 2-deoxyribose spacer. Other spacers are known in the art. See, for example, International Patent Application publication No. WO/2005/012499.

D. Stem Sequence S

In some embodiments, the device further comprises a stem sequence S which, when present, is part of a double stranded portion of the device. Stem sequence S is complementary to all or part of sequence S' in the duplex portion of the device, such that stem sequence S hybridizes to sequence S'. In some aspects, stem sequence S and sequence S' form a duplex structure which is stable at a temperature within a range of about 0° C. to about 95° C., about 20° C. to about 95° C., about 37° C. to about 95° C., e.g., within a range of about 40° C. and about 85° C., within a range of about 45° C. and about 80° C., within a range of about 50° C. and about 75° C., within a range of about 60° C. and about 75° C. In certain aspects, stem sequence S comprises a GC content between about 0% to about 100%, or about 70% and about 100%, or between about 80% and about 100%. In particular aspects, the device comprises a first polynucleotide of Structure 2 and a second polynucleotide of Structure 3 and the stem sequence S comprises a GC content between about 0% to about 100%, between about 70% and about 100% or between about 80% and about 100%.

In various aspects, stem sequence S is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 20, about 25, about 30, about 35 about 40, about 45, about 50, about 55, about 60, about 65, about 70, about 75, about 80, about 85 about 90, about 95 or about 100. In other aspects, stem sequence S is from about 5 bases to about 25 bases in length, about 5 bases to about 20 bases in length, or about 5 bass to about 15 bases in length. In other aspects, stem sequence S is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

E. Loop Sequence L

In aspects of the invention wherein the device is a single nucleic acid molecule, loop sequence L is present. Loop sequence L is of sufficient length to allow the single nucleic acid device to fold over on itself and give rise to a hairpin secondary structure wherein stem sequence S, when present, is able to hybridize to sequence S' and product sequence Y is able to hybridize to sequence Y'.

In various aspects, loop sequence L is about 1 base to about 15 bases in length, about 1 base to about 14 bases in length, about 1 base to about 13 bases in length, about 1 base to about 12 bases in length, about 1 base to about 11 bases in length, about 1 base to about 10 bases in length, about 1 base to about 9 bases in length, about 1 base to about 8 bases in length, about 1 base to about 7 bases in length about 1 base to about 6 bases in length, or about 1 base to about 5 bases in length. Alternatively, loop sequence L is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length.

F. Stem Sequence S'

In aspects in which stem sequence S is present in the device, the device further comprises stem sequence S' which, as discussed above, is all or in part complementary to stem sequence S and is part of a duplex region of the device, such that sequence S' hybridizes to stem sequence S. As discussed above, in some aspects, stem sequence S and sequence S' form a duplex structure which is stable at a temperature within a range of about 0° C. to about 95° C., about 20° C. to about 95° C., 37° C. and about 95° C., e.g., within a range of about 40° C. and about 85° C., within a range of about 45° C. and about 80° C., within a range of about 50° C. and about 75° C., within a range of about 60° C. and about 75° C. In certain aspects, sequence S' comprises a GC content between about 0% to about 100%, between about 70% and about 100%, or between about 80% and about 100%. In particular aspects, the device comprises a first polynucleotide of Structure 2 and a second polynucleotide of Structure 3 and the sequence S' comprises a GC content between about 0% to about 100%, between about 70% and about 100% or about 80% and about 100%.

In various aspects, sequence S' is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 20, about 25, about 30, about 35 about 40, about 45, about 50, about 55, about 60, about 65, about 70, about 75, about 80, about 85 about 90, about 95 or about 100. In other aspects, sequence S' is from about 5 bases to about 25 bases in length, about 5 bases to about 20 bases in length, or about 5 bass to about 15 bases in length. In other aspects, sequence S' is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length. In some aspects, sequence S' is the same length as stem sequence S.

G. Sequence Y'

The device also includes sequence Y' which in certain aspects is complementary to product sequence Y. Hybridization of Y' to Y gives rise to a duplex region of the device. In certain aspects, sequence Y' is complementary to product sequence Y over its entire length. In other aspects, sequence Y' is complementary to product sequence Y over only a partial length of sequence Y'.

In some aspects, sequence Y' includes base modifications that increase the stability of the duplex formed between Y and Y' sequences. Examples of such modifications include but are not limited to RNA bases, LNA bases, and PNAs.

Sequence Y', in certain aspects, is from X bases to Y bases in length, wherein X is 1, 2, 3, 4, 5, 6, 7, 8, 9, 10, 11, 12, 13, 14, 15, 16, 17, 18, 19, 20, 21, 22, 23, 24, or 25 and Y is about 30, about 35 about 40, about 45, about 50, about 55, about 60, about 65, about 70, about 75, about 80, about 85 about 90, about 95 or about 100. In other aspects, product sequence Y is about 10 bases to about 75 bases in length. Alternatively, sequence Y' is about 10 bases to about 70 bases, about 10 bases to about 65 bases, about 10 bases to about 60 bases, about 10 bases to 55 bases, about 10 bases to about 50 bases in length, about 10 bases to about 45 bases in length, about 10 bases to about 40 bases in length, about 10 bases to about 35 bases in length, about 10 bases to about 30 bases in length, about 10 bases to about 25 bases in length, about 10 bases to about 20 bases in length or about 10 bases to about 15 bases in length. In various other embodiments, the sequence Y' is 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases, 32 bases, 33 bases, 34 bases, 35 bases, 36 bases, 37 bases, 38 bases, 39 bases, 40 bases, 41 bases, 42 bases, 43 bases, 44 bases, 45 bases, 46 bases, 47 bases, 48 bases, 49 bases, 50 bases, 51 bases, 52 bases, 53 bases, 54 bases, 55 bases, 56 bases, 57 bases, 58 bases, 59 bases, 60 bases, 61 bases, 62 bases, 63 bases, 64 bases, 65 bases, 66 bases, 67 bases, 68 bases, 69 bases, 70 bases, 71 bases, 72 bases, 73 bases, 74 bases, 75 bases, 76 bases, 77 bases, 78 bases, 79 bases, 80 bases, 81 bases, 82 bases, 83 bases, 84 bases, 85 bases, 86 bases, 87 bases, 88 bases, 89 bases, 90 bases, 91 bases, 92 bases, 93 bases, 94 bases, 95 bases, 96 bases, 97 bases, 98 bases, 99 bases, 100 bases or more bases in length. In some aspects, sequence Y' is the same length as product sequence Y.

H. Sequence X

In another embodiment, the device optionally comprises a sequence X which in some aspects hybridizes to a portion of priming sequence P. When in the device, sequence X is positioned 5' to sequence Y'. Without being bound by a specific mechanism, it is postulated that the presence of sequence X increases specificity with which the target sequence hybridizes to the primer sequence P. Alternatively, or in addition, the presence of the sequence X increases the rate and/or degree of dissociation of the extended target sequence from the device once extension of the target sequence is completed. In certain aspects, sequence X hybridizes to the 5' end of P. In another aspect, sequence X hybridizes to at least a portion of primer sequence P. In some aspects, sequence X hybridizes to only a portion of primer sequence P. In some aspects, sequence X hybridizes to only the 5' end of primer sequence P. In still another embodiment, sequence X hybridizes to at least a portion of primer sequence P and to at least a portion of product sequence Y. In some aspects, sequence X hybridizes to only a portion of primer sequence P and only a portion of product sequence Y. In some aspects, sequence X hybridizes to only the 5' end of primer sequence P and to only the 3' end of product sequence Y.

In various embodiments, sequence X does not hybridize to any sequence in the device. In such embodiments, sequence X may be considered as a 5' flap. Without being bound by a specific mechanism, it is postulated that the presence of X increases the rate and/or degree of dissociation of the extended target sequence from the device once extension of the target sequence is completed.

In various embodiments, sequence X is from X bases to Y bases in length, wherein X is 1, 2, 3, 4, or 5 and X is 6, 7, 8, 9, 10, 11, 12, 13, 14, 15, 16, 17, 18, 19, 20 or more. In other aspects, sequence X is about 1 base to about 20 bases, about 1 base to about 15 bases, or about 1 base to about 10 bases. In certain aspects, sequence X is 1, base, 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, or more bases in length.

I. Blocking Group F

The device of the invention optionally includes a blocking group F positioned 3' to the primer sequence P. Blocking group F blocks DNA polymerase extension on primer sequence P, i.e., precludes increasing length of the primer sequence P. When present, the blocking group F in certain aspects is a 3' amino group, a 3' phosphate, or a dideoxynucleotide, a six carbon glycol spacer (and in one aspect the six carbon glycol spacer is hexanediol) and inverted deoxythymidine (dT). The person of ordinary skill in the art will appreciate that any polymerase blocking group can be positioned 3' to priming sequence P. For example, inasmuch as a 3' hydroxyl group is necessary for polymerase activity, the worker of ordinary skill will appreciate that any group other than a 3' hydroxyl at the 3' terminus of primer sequence P will be a useful blocking group.

J. Strand Protection

In some aspects, the device is protected from cleavage by an enzyme. In exemplary aspects, the device comprises one or more non-cleavable bonds in place of a sugar-phosphate bond, e.g., modified internucleotide linkages which are not cleavable by an enzyme. In some aspects, the device comprises one or more non-cleavable bonds including, for example, any of the linkages of a modified polynucleotide containing a modified backbone as described herein. In particular aspects, the one or more non-cleavable bonds, e.g., modified internucleotide linkages, are located 5' to product sequence Y.

III. Physical Properties

In certain aspects, the double stranded region between sequence S and sequence S' is maintained without dissociation during an extension reaction. Alternatively, the double stranded region between sequence S and sequence S' is not maintained without dissociation, but at any instance in time, it is more likely than not that sequence S and sequence S' are in a duplex conformation. The worker of ordinary skill in the art will readily appreciate how to design and synthesize sequence S and sequence S' in order to either maintain double stranded conformation or to insure that the double stranded conformation is more likely to exist at any instance in time over the course of an extension reaction.

For example and without limitation, stability of a duplex region formed between sequence S and sequence S' is increased with a high GC content. Thus, in certain aspects, sequence S and sequence S' have a GC content between about 0% to about 100%, between about 70% and about 100%, or between about 80% and about 100%.

In another example, and with respect to a device of the invention comprising two polynucleotides as set out above, the two polynucleotides are driven toward hybridization in mixtures wherein one polynucleotide is present in a molar excess of the other polynucleotide. In various aspects, the polynucleotide as set out in Structure 3 is present in a 2×, 3×, 4×, 5×, 6×, 7×, 8×, 9×, 10, 20×, 30×, 40×, 50×, 60×, 70×, 80×, 90×, 100×, 200×, 300×, 400×, 500×, 600×, 700×, 800×, 900×, 1000× or greater molar excess compared to the concentration of the polynucleotide set out ion Structure 2 above.

The worker of ordinary skill in the art will appreciate that, in certain aspects, reaction conditions in an extension reaction are modified so as to enhance the likelihood that double stranded regions in a device of the invention are stabilized. Reaction condition parameters that are subject to modification include, for example, salt concentration and pH. In view of the requirement that an extension product eventually will be displaced, or dehybridized, from a device in the reaction mixture and double stranded regions of the device are reformed prior to any further extension reaction, a balance is achieved with respect to temperature of the reaction mixture and stability of either a double stranded region formed between primer sequence P with a target molecule, primer sequence P and product sequence Y with an extension product, product sequence Y with sequence Y', stem sequence S with sequence S', product sequence Y and stem sequence S with sequence Y' and sequence S'.

In some aspects, the interaction between S and S' is interrupted by exposure to denaturing conditions (e.g., about 94° C. to 100° C.) but the interaction is restored upon decreasing the temperature to about 75° C. or below.

IV. Polynucleotides of the Devices

As used herein, the term "polynucleotide" as a target molecule, is used interchangeably with the term oligonucleotide. The term "nucleotide" or its plural as used herein is interchangeable with modified forms as discussed herein and otherwise known in the art. In certain instances, the art uses the term "nucleobase" which embraces naturally-occurring nucleotides as well as modifications of nucleotides that can be polymerized.

Methods of making polynucleotides for a device having a predetermined sequence are well-known in the art. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

In various aspects, methods provided include use of polynucleotides which are DNA, modified DNA, RNA, modified RNA or combinations of the two types. Modified forms of polynucleotides are also contemplated for devices of the invention which include those having at least one modified internucleotide linkage. Modified polynucleotides or oligonucleotides are described in detail herein below.

V. Modified Polynucleotides

Specific examples of modified polynucleotides include those containing modified backbones or non-natural internucleoside linkages. Polynucleotides having modified backbones include those that retain a phosphorus atom in the backbone and those that do not have a phosphorus atom in the backbone. Modified polynucleotides that do not have a phosphorus atom in their internucleoside backbone are considered to be within the meaning of "polynucleotides."

Modified polynucleotides backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotides backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289;

5,618,704; 5,623,070; 5,663,312; 5,633,360; 5,677,437; 5,792,608; 5,646,269 and 5,677,439, the disclosures of which are incorporated herein by reference in their entireties.

In still other embodiments, polynucleotides mimetics wherein both one or more sugar and/or one or more internucleotide linkage of the nucleotide units are replaced with "non-naturally occurring" groups. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., 1991, *Science,* 254: 1497-1500, the disclosures of which are herein incorporated by reference.

In still other embodiments, polynucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are polynucleotides with morpholino backbone structures described in U.S. Pat. No. 5,034,506.

In various forms, the linkage between two successive monomers in the oligo consists of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where RH is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—; —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$S—R)—O—, —O—PO(BH$_3$)—O—, —O—PO(NHR$^N$)—O—, —O—P(O)$_2$—NR"H—, —$NR^H$—P(O)$_2$—O—, —O—P(O,NR$^H$)—O—, —CH=P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—O—P(=O,S)—O—, —O—P(S)$_2$—O—, —$NR^H$P(O)$_2$—O—, —O—P(O,NR$^H$)—O—, —O—PO(R")—O—, —O—PO(CH$_3$)—O—, and —O—PO(NHR$^N$)—O—, where RH is selected form hydrogen and $C_{1-4}$-alkyl, and R" is selected from $C_{1-6}$-alkyl and phenyl, are contemplated. Further illustrative examples are given in Mesmaeker et. al., 1995, *Current Opinion in Structural Biology,* 5: 343-355 and Susan M. Freier and Karl-Heinz Altmann, 1997, *Nucleic Acids Research,* vol 25: pp 4429-4443.

Still other modified forms of polynucleotides are described in detail in U.S. patent application No. 20040219565, the disclosure of which is incorporated by reference herein in its entirety.

Modified polynucleotides also optionally contain one or more substituted sugar moieties. In certain aspects, oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include O[($CH_2$)$_n$O]$_m$CH$_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$]$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., 1995, *Helv. Chim. Acta,* 78: 486-504) i.e., an alkoxyalkoxy group. Other modifications include 2'-dimethylaminooxyethoxy, i.e., a O($CH_2$)$_2$ON(CH$_3$)$_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples herein below.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—$CH_2$—)$_n$ group bridging the 2' oxygen atom and the 4' carbon atom wherein n is 1 or 2. LNAs and preparation thereof are described in WO 98/39352 and WO 99/14226.

Polynucleotides also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzox-azin-2(3H)-one), carbazole cytidine (2H-pyrimido[4,5-b]indol-2-one), pyridoindole cytidine (H-pyrido[3',':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, *Angewandte Chemie, International Edition*, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. No. 3,687,808, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, $N',N'$-ethano-2,6-diaminopurine, 5-methylcytosine (mC), 5-($C^3$-$C^6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, *Nucleic Acids Research*, vol. 25: pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, *Angewandte Chemie*, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

VI. Target Molecules

In various aspects, a target molecule for use with a device of the invention is a single stranded polynucleotide. In another aspect, the target molecule is a double stranded molecule that has an overhanging 3' sequence. In either embodiment, the 3' single strand terminus of the target molecule is sufficiently complementary to a primer sequence P of a device to allow for hybridization to the primer sequence P. In various aspects, the 3' single strand terminus of the target molecule is 100% complementary to primer sequence P of the device, or alternatively, the 3' single strand terminus of the target molecule is less than 100% complementary to primer sequence P of the device.

In various aspects, the target molecule is bound to a support in a way that the 3' terminus of the target molecule is free to hybridize to the primer sequence P of a device. The support in some aspects is a solid support, including, but not limited to, a bead, a plate, a dish, a tube, a capillary tube, a needle, a well, a paper, a slide, a chip, a filter, a membrane, and the like. In certain aspects, the solid support comprises one or more surfaces comprising or coated with plastic (e.g., polypropylene, polystyrene), glass, nylon, nitrocellulose, polyvinylidene fluoride, and the like.

VII. Compositions and Uses

A. Single Extension Products

Compositions are provided comprising one or more devices as described herein. In one aspect, compositions of the invention comprise two or more devices wherein all of the devices are the same, i.e., the product sequence Y in all of the devices in the composition are the same and all devices extend the target molecule to have the same added sequence.

B. Multiple Extension Products

In another aspect, compositions are provided wherein at least two devices in the composition are not the same, i.e., product sequence Y in one device is different from product sequence Y in a second device such that at least two devices in the composition extend the target molecule to have difference added sequences.

In one aspect of this type of composition, it is contemplated that the two devices in the composition extend the same target molecule consecutively, wherein the product of the first extension reaction results in a 3' extension sequence which makes this first extension product amenable to further extension with a second device in the composition.

To explain this composition in terms of individual sequences in the devices by way of example and without limitation, a composition is provided with two devices; the first device has a primer sequence $P_1$ and a product sequence $Y_1$, and a second device has a primer sequence $P_2$ and a product sequence $Y_2$. In the presence of a target molecule having a 3' terminus complementary to a primer sequence $P_1$ in a first device, the target molecule is extended to have a sequence complementary to $Y_1$ ($cY_1$) in a first extension product. This first extension product having a 3' sequence complementary to $Y_1$ ($cY_1$) is able to be further extended if $cY_1$ is complementary to a primer sequence $P_2$ in a second device, thereby allowing for production of a second extension product wherein the $cY_1$ sequence from the first extension reaction is further extended to include a sequence complementary to product sequence $Y_2$ ($cY_2$) added by the second device. In this type of reaction the final extension product, after two separate extension reactions, will have a 3' sequence which is complementary to primer sequence P1 (cP1) followed at the 3' terminus with sequences $cY_1$ and $cY_2$, which are complementary to sequences $Y_1$ and $Y_2$, respectively.

The worker of ordinary skill in the art will readily appreciate that any number of different devices can be provided in a composition such that the extension product of a first extension reaction can be rendered amenable to further extension by a second device, the extension product from a second extension reaction with a second device can be rendered amenable to further extension by a third device, and so forth. Any number of devices is contemplated for compositions of the invention.

C. Single Stranded Target Molecule Extension

The devices and compositions provided herein are designed for the purpose of extending target molecules, e.g., single stranded target molecules, target molecules comprising at least a portion which is single stranded. Accordingly, the invention provides a method of extending a single stranded target molecule comprising contacting the single stranded target molecule with an extension reaction mixture comprising (i) a device in accordance with the present disclosures or a composition comprising a device in accordance with the present disclosures, (ii) a polymerase, and (iii) free nucleotides, whereupon an extension reaction product is generated, wherein an extension product of the reaction comprises the single stranded target molecule with a 3' sequence complementary to product sequence Y of the device.

The extension reaction mixture used in the method of extending a single stranded target molecule may comprise any of the devices described herein and, in some aspects, the choice of device used in the method will depend on the type of extension reaction product desired or the ultimate goal or purpose of the extension of the target molecule, as further discussed herein. In exemplary aspects, the device is a polynucleotide of Structure 1. In other exemplary aspects, the device is a polynucleotide pair or polynucleotide set comprising a first polynucleotide of Structure 2 and a second polynucleotide of Structure 3.

In some aspects of the method, the extension reaction mixture comprises a device, wherein product sequence Y consists of an additional sequence A, which is not identical to priming sequence P, and additional sequence A is about 10 bases to about 50 bases (e.g., about 20 bases to about 30 bases) in length, and the extension product generated upon execution of the method includes a 3' terminal sequence complementary to sequence A.

In some aspects of the method, the extension reaction mixture comprises a device, wherein product sequence Y consists of a sequence $P_Y$ which is identical to primer sequence P of the device, whereupon the target molecule sequence is complementary to the primer sequence P, and the reaction product has a 3' terminal sequence that is complementary to the primer sequence P.

In some aspects, the extension reaction mixture comprises a device, wherein product sequence Y of the device comprises sequence $P_Y$ which is identical to primer sequence P of the device and further comprises a tag sequence T which is different from the sequence of sequence $P_Y$ and sequence T is located 3' to $P_Y$.

In some aspects, the extension reaction mixture comprises a plurality of devices in accordance with the present disclosures, wherein the plurality comprises at least three subsets of devices, wherein each device of a subset comprises a sequence Y sequence which is (i) the same as sequence Y of another device of the same subset and (ii) different from sequence Y of a device of another subset of the plurality, wherein the extension product has a 3' terminus which comprises a sequence which is complementary to each sequence Y of the plurality, e.g., wherein the extension product has a 3' terminus which comprises a sequence which is complementary to the final sequentially-added tandem sequence Y of the plurality.

With regard to the extension reaction mixture used in the methods provided herein, the polymerase is any enzyme whose central function is to catalyze the polymerization of a new polynucleotide, such as DNA or RNA, against an existing template. In exemplary aspects, the polymerase is a DNA polymerase (e.g., DNA polymerase I, DNA polymerase II, DNA polymerase III holoenzyme, DNA polymerase IV), an RNA polymerase (e.g., RNA polymerase I, RNA polymerase II, RNA polymerase III, T7 RNA polymerase), or a combination thereof. In some aspects, the polymerase is a strand displacement polymerase, e.g., a polymerase which exhibits strand displacement activity. In some aspects, the strand displacement activity is limited. In alternative aspects, the strand displacement activity is strong. In some aspects, the polymerase is a DNA polymerase with limited or strong strand displacement activity (e.g., Klenow fragment of DNA polymerase I, Klenow fragment of DNA polymerase I (exo-), Phi29 DNA polymerase, Sequenase™ II, Large fragment of Bst DNA polymerase, DisplaceAce™ DNA polymerase, MMLV reverse transcriptase, AMV reverse transcriptase, Taq DNA polymerase (5' exo-), Vent DNA polymerase, Ven(exo-) DNA polymerase, Deep Vent DNA polymerase, Deep Vent DNA polymerase (exo-), and the like. The polymerase in some aspects is any of those described further in the section entitled "Kits."

With regard to the extension reaction mixture used in the methods provided herein, the free nucleotides may be any free (e.g., unpolymerized) nucleotides known in the art, including, but not limited to any of the naturally-occurring nucleotides, dATP, dCTP, dTTP, dUTP, dGTP, and modified forms discussed herein, e.g., nucleotides comprising modified bases, nucleotides of any of the modified polynucleotides. The free nucleotides in some aspects is a combination of different types of nucleotides optionally in admixture. In exemplary aspects, the combination comprises dATP, dCTP, dTTP, dGTP, and optionally, dUTP. In some aspects, the combination comprises each type of free nucleotide in equal amounts, e.g., equimolar amounts. In some aspects, one or more free nucleotides is in limiting amounts, and in some aspects, the one or more free nucleotides present in the extension reaction mixture is the complementary nucleotide of internal replication blocking group R. By "limiting amounts" as used herein refers to an amount which is at least or about 2-fold, at least or about 3-fold, at least or about 5 fold, at least or about 10-fold, at least or about 20-fold, at least or about 30-fold, at least or about 50-fold, at least or about 100-fold less than the amount of another free nucleotide.

In exemplary aspects, the method of extending a single stranded target molecule provided herein is carried out under conditions suitable for an extension reaction to take place such that an extension reaction product is generated. Such conditions are known in the art. See, for example, Sambrook et al., *Molecular Cloning, A Laboratory Manual*, 3$^{rd}$ ed., Cold Spring Harbor Laboratory Press, Cold Spring Harbor, N.Y., 2001; White, Bruce A., *PCR Cloning Protocols*, Humana Press, Totowa, N.J., 1997; Dieffenbach and Dveksler, *PCR Primer: A Laboratory Manual*, Cold Spring Harbor Laboratory Press, Cold Spring Harbor, N.Y., 2003; Keller and Manak, *DNA Probes: background, applications, procedures*, 2$^{nd}$ ed., Macmillan Press, 1993; Lee et al., *Nucleic Acid Amplification Technologies*, Eaton Publishing, Cambridge, Mass., 1997.

The method, in some aspects, is carried out under substantially isothermal conditions. As used herein, the term "substantially isothermal conditions" refers to conditions in which a single temperature, t, is essentially maintained and includes conditions in which the temperature is maintained within a range of about $-10\%$ t ° C. to about $+10\%$ t ° C. In particular aspects, the method is carried out under substantially isothermal conditions and the method is carried out at a temperature within a range of about 0° C. to about 95° C., about 20° C. to about 95° C., about 37° C. to about 95° C., about 60° C. to about 75° C.

In alternative aspects, the method is not carried out under substantially isothermal conditions, and the method comprises one or more thermal cycles. In specific aspects, the method comprises one or more steps carried out at a first temperature and one or more steps carried out at a second temperature, wherein the second temperature is at least or about 25° C. greater the first temperature. In exemplary aspects, the first temperature is within a range of about 60° C. to about 75° C. and the second temperature is within a range of about 85° C. to about 100° C. In some aspects, the method comprises a dissociation step in which the polymerase dissociates from the device at the second temperature.

D. Extension Product Detection

In some aspects, the method of extending a single stranded target molecule provided herein comprises one or more additional steps. In exemplary aspects, the method further comprises detecting the extension reaction product and optionally quantifying the extension reaction product.

In one aspect, tag sequence T in sequence Y allows for extension of the target molecule to include a sequence complementary to sequence T (cT), and the sequence cT in the extension product is designed to bind a probe. In one aspect, the probe is a sequence specific probe. In another aspect, the probe is, or includes, a detectable label. In aspects wherein a probe binds sequence cT in the extension product but not sequence $cP_Y$ in the extension product, multiple copies of the sequence $cT\text{-}cP_Y$ are added to the target single strand polynucleotide, with a probe optionally binding to each copy of the $cT\text{-}cP_Y$ extension product in the cT portion of the sequence.

In another aspect, additional sequence A of the device allows for extension of the target molecule to include a sequence complementary to sequence A (cA), and the sequence cA in the extension product is designed to bind a probe. In one aspect, the probe is a sequence specific probe. In another aspect, the probe is, or includes, a detectable label.

The probe may be any length suitable for hybridizing to the extension reaction product, e.g., via sequences cT or cA. In some aspects, the probe is the same length as sequence T or sequence A of the device. In particular aspects, the probe is about 10 to about 50 bases long, e.g., about 15 to about 40, about 20 to about 30 bases long.

In some aspects, the probe is a single stranded polynucleotide. In other aspects, at least a portion of the probe forms a duplex structure. For example, in some aspects, at least a portion of the probe forms a hairpin structure, which in certain aspects unfolds (e.g., becomes single-stranded) and subsequently binds to the extension reaction product. Accordingly, in some aspects, the probe is a molecular beacon.

The detectable label of the probe may be any of those known in the art, including, but not limited to, a radioisotope (e.g., $^{133}$Barium, $^{109}$Cadmium, $^{57}$Co, $^{60}$Co, $^{152}$Europium, $^{54}$Mn, $^{22}$Na, $^{65}$Zn, $^{99m}$Technetium, $^{90}$Strontium, $^{204}$Thallium, $^{14}$C, $^{32}$P, $^{125}$I), a fluorophore (e.g., hydroxycoumarin, methoxycoumarin, aminocoumarin, FAM, 6-carboxyfluorescein, Alexa fluor 430, Alexa fluor 488, Alexa fluor 532, Alexa fluor 546, Alexa fluor 555, Alexa fluor 568, Alexa fluor 594, Alexa fluor 633, Alexa fluor 660, Alexa fluor 680, fluorescein, HEX, Cy3, TRITC, R-phycoerythrin, rhodamine red-X, tamara, Rox, texas red, allophycocyanin, TruRed, Cy2, Cy3, Cy3.5 581, Cy5, Cy5.5, Cy7) and an elemental particle (e.g., gold, copper, silver), and the like.

In some aspects, the detectable label permits quantification of the extension reaction product. In exemplary aspects, the amount of radioactivity of a radioisotope or the amount of fluorescence of a fluorophore correlates with the amount of the extension reaction product or correlates with the length of the extension reaction product. In the latter case, the amount of radioactivity or fluorescence in some aspects correlates with n, when the extension reaction product comprises a structure 5'-cP-$(cT\text{-}cP_Y)_n$-3'.

In another aspect, compositions provided comprise one or more probes or markers that detect extension products produced by the devices. In one aspect a probe or marker is provided which binds to an extension product complementary to a product sequence Y (cY). In one aspect, the probe or marker does not bind to Y' which is typically identical to the 3' terminus of the product of an extension reaction. In one aspect, the probe or marker binds only to the extension product in order to detect products of the extension reaction. In one embodiment, the probe or marker binds to the 3' terminus of the extension product.

A probe or marker for compositions includes one which is detectable only when it binds to the product of an extension reaction. In one aspect, the probe or marker produces a signal when bound to the extension product. In another aspect the probe or marker signal is quenched when the probe or marker is not bound to the extension product.

In some aspects, the probe or marker is a molecular beacon comprises a quenching moiety, which prevents emission of a signal from the detectable label until the probe or molecular beacon is hybridized to its target, e.g., hybridized to the extension reaction product. Quenching moieties are known in the art. See, for example, Livak et al., *Genome Res.* 4: 357-

362 (1995). Non-limiting examples of quenchers contemplated for use in practice of the methods of the invention include Black Hole Quencher 1, Black Hole Quencher-2, Iowa Black FQ, Iowa Black RQ, Zen quencher, and Dabcyl. G-base.

In view of the above discussion, in some aspects, the methods provided herein comprise one or more steps for detection and/or quantification of the extension reaction product using one or more probes, molecular beacons or a combination thereof. Accordingly, in some aspects, the compositions and kits provided herein comprise a probe, molecular beacon, or a combination thereof, such as any of those described herein.

E. Product Amplification

In a method utilizing one or more devices of the invention, a target molecule and at least one device are provided. The target molecule is extended in a reaction that results in the target molecule having a sequence added that is complementary to product sequence Y in the device. In one aspect, the sequence added to the target molecule has a cleavage site at the junction between the sequence complementary to primer sequence P (cP) and the product sequence Y (cY), and also introduces a sequence $cP_Y$ 3' to cY wherein $cP_Y$ is complementary to primer sequence P of the device. After the extended product of the reaction is dissociated from the device, the extension product is cleaved at the cleavage site resulting in two products which are again extended with device in the reaction mixture. The process is repeated a desired number of time to exponentially amplify the target sequence.

In one aspect, the reaction mixture also includes a probe as described here which is able to bind to and detect the amplification product. The probe in certain aspects comprises a detectable label, e.g., any of those described herein, which allows for detection and quantification of the amplification product.

In additional or alternative aspects, the reaction mixture further comprises an enzyme which cleaves an extension product, e.g., at a cleavage site at the junction between the sequence complementary to primer sequence P (cP) and the product sequence Y (cY). In exemplary aspects, the cleavage site comprises a dU-base. Accordingly, the kits and compositions provided herein in some aspects comprises an enzyme which cleaves an extension product.

VIII. Applications

The worker of ordinary skill in the art will appreciate that the device of the invention has a multitude of uses in applications that extension of a single stranded polynucleotide, or a single stranded terminal region of a double stranded polynucleotide (whether overlapping or transiently single stranded), is desired.

Tagging Compounds

For example, applications include those wherein a polynucleotide which has a sufficiently long single strand region that hybridizes to primer sequence P, or can be denatured to provide a single strand region that hybridizes to primer sequence P, is extended with a unique and/or detectable sequence. Unique and/or detectable sequence includes those that will hybridize to a detection sequence and/or bind to a specific label. In these and other applications, the target sequence is, in various embodiments, (i) in solution, (ii) associated with or complexed with a second compound, or (iii) immobilized, e.g., to a solid support. Second compounds include any compound that includes a single strand polynucleotide which hybridizes to primer sequence P, whether the presence of the single strand polynucleotide is naturally-occurring (i.e., found in nature) in association with the compound, or whether the single strand polynucleotide has been associated with the compound and is not found in nature. The association between the single strand target and the compound is in certain aspects covalent and in other aspects the association between the single strand target and the compound is non-covalent.

In exemplary aspects, the second compound is any molecule (chemical or biochemical, naturally-occurring or non-coded) which is different from the devices and the target molecules. Exemplary second compounds include but are not limited to a protein, a peptide, an amino acid, a lipid, a carbohydrate, an oligonucleotide or polynucleotide, (e.g., a gene, a chromosome, a DNA, a microRNA, a messenger RNA), a polymer, a cell, a virus, a bacteria, a prion, a toxin, and the like. Amplification and detection of the second compound may be accomplished using the devices of the present disclosures in accordance with the descriptions provided herein.

In aspects wherein the single strand target molecule is immobilized, the single strand target is, in various aspects, associated with a particle, cell, virus, sub-cellular organelle or surface. The association between the single strand target and particle or surface is in certain aspects covalent and in other aspects the association between the single strand target and particle or surface non-covalent. The single strand target polynucleotide is in some aspects randomly placed when immobilized and in other aspects, the single strand target molecule is immobilized in a specific location. In one aspect, the single strand target molecule is arrayed when immobilized. In aspects wherein the single strand target molecule is arrayed, the arrayed single strand target molecule all have the same sequence, and in other aspects, the arrayed single strand target molecules do not have the same sequence.

The immobilized single strand target polynucleotide is in certain aspect immobilized in multiple copies wherein all single strand target polynucleotides have the same or essentially the same sequence. In other aspects, a single strand target polynucleotide is immobilized with at least one other single strand target polynucleotide that has a different sequence. Similarly, in aspects wherein the single strand target molecule is arrayed, the arrayed single strand target molecule all have the same sequence, and in other aspects, the arrayed single strand target molecules do not have the same sequence.

In particular aspects, the target sequence is immobilized to a surface of a solid support. The solid support may be any of those described herein. In some aspects, the compositions or kits provided herein comprise a solid support to which one or more target sequences are immobilized. Accordingly, in some aspects, the method of extending a single stranded target molecule comprises contacting a solid support comprising the single stranded target molecule immobilized thereto, with the extension reaction mixture.

Diagnostic Methods

Accordingly, the devices of the present disclosures are useful in diagnostic methods. In exemplary embodiments, the devices are used in methods of detecting gene mutations, e.g., point mutations, deletions, chromosomal aberrations, trinucleotide repeat disorders, the absence or presence of a gene or the presence of multiple copies of a gene or chromosome. The method are used in various aspects to diagnose a medical condition or disease, e.g., cancer, genetic disorder (e.g., 22q11.2 deletion syndrome, Angelman syndrome, Canavan disease, Celiac disease, Charcot-Marie-Tooth disease, color blindness, Cri du chat, cystic fibrosis, Down syndrome, Duchenne muscular dystrophy, haemochromatosis, haemophilia, Klinefelter's syndrome, neurofibromatosis, phenylketonuria, polycystic kidney disease, Prader-Willi syndrome, sickle cell disease, Tay-Sachs disease, Turner syndrome, and the like.

In some aspects, the diagnostic method is an in situ diagnostic method. In exemplary embodiments, the diagnostic method comprises using the devices of the present disclosures for fluorescent in situ hybridization (FISH) copy number analysis. In particular aspects, one or more target sequences are immobilized in part to a solid support. In certain aspects, the target sequence comprises a single stranded portion which is not immobilized to the solid support and hybridizes to primer sequence P of a device of the present disclosures. In some aspects, the target sequence is extended and amplified in accordance with the teachings provided herein and the amplification product is detected and optionally quantified using a probe, e.g., a molecular beacon, comprising a detectable label.

Protein Microarray Analysis

The devices of the present disclosures are also useful in protein analysis using antibody arrays. In exemplary embodiments, the device is used to detect the presence or absence of one or more proteins of a protein mixture, and optionally to quantify the protein(s) present in the protein mixture and/or to identify the protein(s) present in the protein mixture. The protein mixture may be for example a lysate of diseased cells, e.g., cancer cells, and the presence/absence of the protein(s) in the protein mixture, as well as the quantity and identification of the protein(s) are indicative of the disease in a subject. In exemplary aspects, proteins of a protein mixture are labeled with a mixture of single stranded target molecules, and the labeled proteins are contacted with an array of known antibodies. The unbound components of the protein mixture are washed off of the array and antibody-protein complexes are detected using the devices of the present disclosures in combination with probes which bind to the extension products and which comprise a detectable label.

Synthesis of Polynucleotides and Arrays Comprising the Same

The devices of the present disclosures are further useful in methods of synthesizing polynucleotides. In exemplary embodiments, the device is used for making a polynucleotide comprising a sequence which is complementary to Y (cY). In certain aspects, the devices of the present disclosures are used in a method of solid phase gene synthesis and the devices are provided as a composition comprising a plurality of subsets of devices, each subset comprising multiple copies of a device, each subset of devices comprising a sequence Y which is different from that of devices of other subsets. In some aspects, the composition is in accordance with those described under the section entitled "Multiple extension products."

In alternative aspects, the devices of the present disclosures are used to construct an array of oligonucleotides. In exemplary aspects, a solid support comprising an array of immobilized single stranded target molecules is contacted with one or more devices or compositions comprising the same and a polymerase. The devices bind through their primer sequence P to the single stranded target molecule and, with the activity of the polymerase, extend the length of the single stranded target molecules, as described herein, such that the single stranded target molecules comprise the complementary sequence of Y of the device. Multiple rounds of extension is carried out in some aspects with different devices in accordance with the descriptions provided herein under the section entitled "Multiple extension products."

Further applications of the devices, compositions, and kits of the present disclosures are provided herein in EXAMPLES.

IX. Kits

The invention further provides kits comprising a device of the invention and instructions for using the device in an extension reaction which extends a target molecule. In certain aspects the target molecule is a single stranded molecule. In other aspects, the target molecule is double stranded with a 3' overhanging end that is complementary to a primer sequence P in a device in the kit.

In some aspects, the kit further comprises a polymerase and/or free nucleotides. The polymerase is any enzyme whose central function is to catalyze the polymerization of a new polynucleotide, such as DNA or RNA, against an existing template. In exemplary aspects, the polymerase is a DNA polymerase (e.g., DNA polymerase I, DNA polymerase II, DNA polymerase III holoenzyme, DNA polymerase IV), an RNA polymerase (e.g., RNA polymerase I, RNA polymerase II, RNA polymerase III, T7 RNA polymerase), or a combination thereof. In some aspects, the polymerase is a naturally-occurring polymerase, such as, for example, *Thermus aquaticus* (Taq) polymerase, terminal deoxynucleotidyl transferase, reverse transcriptase (e.g., HIV reverse transcriptase).

In alternative embodiments, the polymerase is a genetically-engineered polymerase, which does not naturally occur in or is non-native to any living organism. The genetically-engineered polymerase, in exemplary aspects, represents a naturally occurring polymerase with one or more amino acid modifications that modify one or more aspects of the polymerase. The genetically modified polymerase in some aspects is a mutant of a naturally occurring polymerase that exhibits increased strand displacement activity and/or increased dissociation from the template strand upon completion of the polymerization activity.

In specific aspects, the kit comprises a 5' exonuclease-minus polymerase.

In some aspects, the kit comprises a strand displacement polymerase, e.g., a polymerase which exhibits strand displacement activity. In some aspects, the strand displacement activity is limited. In alternative aspects, the strand displacement activity is strong. In some aspects, the polymerase is a DNA polymerase with limited or strong strand displacement activity (e.g., Klenow fragment of DNA polymerase I, Klenow fragment of DNA polymerase I (exo-), Phi29 DNA polymerase, Sequenase™ II, Large fragment of Bst DNA polymerase, DisplaceAce™ DNA polymerase, MMLV reverse transcriptase, AMV reverse transcriptase, Taq DNA polymerase (5' exo-), Vent DNA polymerase, Ven(exo-) DNA polymerase, Deep Vent DNA polymerase, Deep Vent DNA polymerase (exo-), and the like.

In still other non-limiting examples of enzymes that may be used to practice the present invention, to the extent they lack exonuclease activity, they can be modified to remove exonuclease activity, or any inherent exonuclease activity they possess can be blocked by features of the nanosynthesizer, include but are not limited to Deep VentR™ DNA Polymerase, LongAmp™ Taq DNA Polymerase, Phusion™ High-Fidelity DNA Polymerase, Phusion™ Hot Start High-Fidelity DNA Polymerase, VentR® DNA Polymerase, DyNAzyme™ II Hot Start DNA Polymerase, Phire™ Hot Start DNA Polymerase, Phusion™ Hot Start High-Fidelity DNA Polymerase, Crimson LongAmp™ Taq DNA Polymerase, DyNAzyme™ EXT DNA Polymerase, LongAmp™ Taq DNA Polymerase, Phusion™ High-Fidelity DNA Polymerase, Phusion™ Hot Start High-Fidelity DNA Polymerase, Taq DNA Polymerase with Standard Taq (Mg-free)

Buffer, Taq DNA Polymerase with Standard Taq Buffer, Taq DNA Polymerase with ThermoPol II (Mg-free) Buffer, Taq DNA Polymerase with ThermoPol Buffer, Crimson Taq™ DNA Polymerase, Crimson Taq™ DNA Polymerase with (Mg-free) Buffer, Phire™ Hot Start DNA Polymerase, Phusion™ High-Fidelity DNA Polymerase, VentR® (exo-) DNA Polymerase, Phire™ Hot Start DNA Polymerase, Phusion™ High-Fidelity DNA Polymerase, Phusion™ Hot Start High-Fidelity DNA Polymerase, Hemo KlenTaq™, Deep VentR™ (exo-) DNA Polymerase, Deep VentR™ DNA Polymerase, DyNAzyme™ EXT DNA Polymerase, Hemo KlenTaq™, LongAmp™ Taq DNA Polymerase, Phusion™ High-Fidelity DNA Polymerase, Bst DNA Polymerase, Full Length, Taq DNA Polymerase with ThermoPol Buffer, 9°Nm DNA Polymerase, Crimson Taq™ DNA Polymerase, Crimson Taq™ DNA Polymerase with (Mg-free) Buffer, Deep VentR™ (exo-) DNA Polymerase, DyNAzyme™ EXT DNA Polymerase, DyNAzyme™ II Hot Start DNA Polymerase, Hemo KlenTaq™, Phusion™ High-Fidelity DNA Polymerase, Phusion™ Hot Start High-Fidelity DNA Polymerase, *Sulfolobus* DNA Polymerase IV, Therminator™ γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, Large Fragment, DNA Polymerase I (*E. coli*), T4 DNA Polymerase, T7 DNA Polymerase (unmodified), Terminal Transferase, Reverse Transcriptases, and *E. coli* Poly(A) Polymerase In some aspects, the polymerase is a thermostable polymerase. In alternative aspects, the polymerase is a non-thermostable polymerase. In some aspects, the polymerase is a mesophilic polymerase. In some aspects, the polymerase is thermostable at a temperature within about 0° C. to about 95° C., about 20° C. to about 95° C., about 37° C. to about 95° C., or about 60° C. to about 75° C.

In some aspects, the polymerase dissociates from the device when in contact with replication blocking group R. In certain aspects, the polymerase dissociates from the device when in contact with replication blocking group R under substantially isothermal conditions. In exemplary aspects, the polymerase dissociates from the device when in contact with replication blocking group R at a temperature within a range of about 0° C. to about 95° C., about 20° C. to about 95° C., about 37° C. to about 95° C., or about 60° C. to about 70° C.

In some aspects, the kit comprises additional molecules that increase the overall efficiency of the extension reactions. In exemplary aspects, the kit comprises a chaperone strand displacement molecule, e.g., a helicase, a transferase, or a single-stranded binding protein. In other exemplary aspects, the kit comprises at least two polymerases, wherein at least one polymerase is a proofreading polymerase, e.g., a proofreading polymerase that removes bases from the single stranded target molecule that are added via one or more non-template addition reactions. In still other aspects, the kit further comprises an enzyme which cleaves a reaction product.

In some aspects, the kit comprises a molecular beacon comprising a detectable label and a sequence which hybridizes to an extension product of an extension reaction. In exemplary aspects, the molecular beacon forms a hairpin structure when not hybridized to the product.

In some aspects, the kit comprises a probe and the probe optionally comprises a detectable label. In other aspects, the kit further comprises as described herein. The following examples are given merely to illustrate the present invention and not in any way to limit its scope.

EXAMPLES

Example 1

The devices of the present disclosures are prepared, in one aspect by chemical synthesis methods that are well known and routinely practiced in the art. Commercial facilities are widely available for synthesis methods of this type.

Example 2

This example describes an exemplary method of extending a single stranded primer extension.

Using a primer of the sequence Y 5'GGA GAG GGA GAA GGG 3' (SEQ ID NO: 1) with a Structure I device capable of extending additional sequence Y comprising the sequence: 5'-AAA GGA GAG GGA GAA GGG CTC CGT ACC GGC CGC TTT TTT GCG GCC GGT ACG GAG CCC TTC TCC CTC TCC CCC TTC TCC CTC TCC-3'(SEQ ID NO: 2), isothermal single stranded primer extension produces a concatamer of sequence Y under the following reaction conditions: 30 minutes at 65° C. containing 20 mM Tris-HCl, 10 mM (NH$_4$)$_2$SO$_4$, 10 mM KCl, 2 mM MgSO$_4$, 0.1% Triton X-100, 200 uM dGTP, 200 uM dATP and containing 10 pmol of primer, 1 pmol of Structure I Y device and 8U Bst DNA Polymerase, large fragment. Additionally, primer Y can be incubated under identical conditions with a Structure I device capable of extending sequence AY comprising the sequence: 5'-AAA AAA GAG GAG AGG GGA AAG GAG AGG GGA GAG GGA GAA GGG CTC CGT ACC GGC CGC TTT TTT GCG GCC GGT ACG GAG CCC TTC TCC CTC TCC CCT CTC CTT TCC CCT CTC CTC TTT CCC TTC TCC CTC TCC-3' (SEQ ID NO: 3) to generate a YA concatamer sequence by isothermal single strand primer extension.

Example 3

This example describes a method for array-based polynucleotide detection and analysis using the devices of the present disclosures.

A plurality of stem-loop probes, each probe of which comprises (i) a sequence which hybridizes to a target polynucleotide and (ii) a sequence that hybridizes to primer sequence P of a device of the presence disclosures, is immobilized onto a solid support in an arrayed fashion to provide a microarray. Each probe forms stem loop structure when not in contact with its target polynucleotide. One end of the stem-loop probe is immobilized to the solid support while the other end comprises the sequence which hybridizes to primer sequence P of the device of the present disclosures. The portion in between forms the stem loop structure when not in contact with the target polynucleotide or forms a duplex structure with the target polynucleotide when present. The end comprising the sequence which hybridizes to primer sequence P of the device is accessible to binding to the device only when the target polynucleotide is bound and the stem-loop probe is not forming a stem loop structure. The microarray is contacted with a mixture of polynucleotides comprising non-target polynucleotides and incubated under conditions that permit target polynucleotides to hybridize to the appropriate stem loop probe. Unhybridized components of the mixture are optionally washed off of the array. Devices of the present disclosures having a primer sequence P which binds to the appropriate end of the stem-loop probes are contacted with the microarray and a polymerase and free nucleotides are added for single stranded primer extension reaction(s). Fluorescently labeled probes which bind to the extension reaction products are added to the array and the fluorescent signal, which represents the presence of a target polynucleotide, is detected.

This example demonstrated a microarray nucleic acid analysis based on the hybridization of DNA or RNA to stem-loop array probes that change their conformation upon target polynucleotide binding, which triggers the amplification process mediated by the devices of the present disclosures. This method provides a novel combination of the array probe design and the signal amplification detection method for sensitive and specific detection of unlabeled nucleic acids on microarrays for diagnostic and research applications. This methodology may be applied to molecular diagnostics, forensics, and detection of biohazards, e.g., biological warfare.

In accordance with the foregoing, in some aspects, a composition or kit comprising the devices of the present disclosures further comprises an array as described in this example.

Example 4

This example describes a method for multiple polynucleotide sample analysis using the devices of the present disclosures.

A sample DNA (DNA1) and a control DNA (DNA2) are incubated with a primary set of devices of the present disclosures to extend each of DNA1 and DNA2 to comprise a universal sequence U at the 3' end of DNA1 or DNA2 (e.g., DNA1-U and DNA2-U). Each device of the primary set used in this method comprises a primer sequence P comprising a random sequence of 8-12 bases and a product sequence Y comprising an additional sequence A, wherein A comprises a complementary sequence of U (cU).

After formation of DNA1-U and DNA2-U, a secondary set of devices are used for further extension. The secondary set comprises devices for DNA1 which differ from the devices for DNA2, in that the product sequence Y comprises a tag sequence T that is different for each of DNA1 and DNA2. The Y sequence of the devices for DNA1 comprises $T_1$-$P_Y$, whereas the Y sequence of the devices for DNA2 comprises $T_2$-$P_Y$. The $P_Y$ of the devices for DNA1 are the same as that for DNA2—the $P_Y$ sequence is the same as P, which is complementary to U. Upon n rounds of extension using the second set of devices, DNA1 comprises a sequence $cP$-$(cT_1$-$cP_Y)_n$ and DNA2 comprises a sequence $cP$-$(cT_2$-$cP_Y)_n$. The extension products of DNA1 and DNA2 generated with the secondary set of devices are contacted with an array. Unbound components are washed off of the array. The arrays are contacted with probes that comprises a detectable label and that hybridize to $cT_1$ or $cT_2$. The array is washed and the signals from the detectable labels are detected. Differences between the signals may be identified and correlated with DNA1 or DNA2 based on the position of the signal on the array and/or by the use of probes having different signals.

In some aspects, the above method is carried out using 4 different DNA molecules: DNA1, DNA2, DNA3, and DNA4. Each DNA molecule is extended using a primary set of devices of the present disclosures in accordance with the above to comprise a U sequence. DNA1-U, DNA2-U, DNA3-U, and DNA4-U are contacted with a second set of devices comprising a unique subset of devices for each DNA molecule. As essentially described above, the device for DNA1 comprises a tag sequence T1, the device for DNA2 comprises a tag sequence T2, the device for DNA3 comprises a tag sequence T3, and the device for DNA4 comprises a tag sequence T4. Upon n rounds of extension using the second set of devices, DNA1 comprises a sequence $cP$-$(cT_1$-$cP_Y)_n$, DNA2 comprises a sequence $cP$-$(cT_2$-$cP_Y)_n$, DNA3 comprises a sequence $cP$-$(cT_3$-$cP_Y)_n$, and DNA4 comprises a sequence of $cP$-$(cT_4$-$cP_Y)_n$.

The extended DNA molecules are hybridized to an array and the array is washed stringently. In some aspects, the array is contacted with a first probe comprising a first detectable label, wherein the first probe hybridizes to cT1 of DNA1. The unbound probe is washed off the array and the signal from the first probe is detected. At the same that time the signal from the first probe is quenched, the array is contacted with a second probe comprising a second detectable label, wherein the second probe hybridizes to cT2 of DNA2. These steps of probe addition, signal detection, and probe quenching at the same time a subsequent probe is added to the array are repeated with the appropriate probe until the signal from the fourth probe is detected.

This example demonstrated a multiplexed DNA microarray hybridization analysis that is based on adding specific DNA repeat sequences to different DNA samples using specialized devices of the present disclosures, pooling the samples, hybridizing the pooled sample to a single microarray, and then recovering information on individual DNA samples by sequential hybridization-depletion reaction that involves the repeat-specific fluorescently labeled oligonucleotide probes and quenchers. This method provides a novel DNA microarray analysis tool that dramatically reduces the array analysis cost, improves the multiple sample data comparison, and increases the throughput of the microarray analysis. This method uses indirect rather than direct labeling DNA method.

What is claimed is:

1. A device for extension of a single stranded target molecule, wherein the device is a polynucleotide comprising Structure 1:

Structure 1:

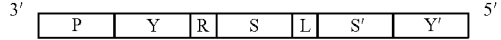

wherein:

P is a primer sequence through which at least the 3' end of the target molecule hybridizes to the device;
Y is product sequence;
R is replication blocking group;
S is a stem sequence;
L is a loop region;
S' is a sequence which hybridizes to S;
Y' is a sequence which hybridizes to Y; and
wherein each of S and S' is optionally present in the device, wherein the presence of S' is dependent on the presence of S in the device,
wherein Y, R, S, L, S', and Y' form a hairpin structure,
wherein Y comprises or consists of a sequence $P_Y$ which is identical to priming sequence P.

2. A device for extension of a single stranded target molecule, the device comprising a first polynucleotide of Structure 2:

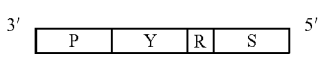

and a second polynucleotide of Structure 3:

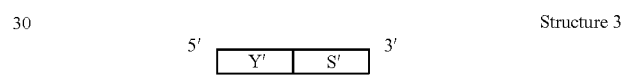

wherein:

P is a primer sequence through which at least the 3' end of the target molecule hybridizes to the device;
Y is product sequence;
R is replication blocking group;
S is a stem sequence;
Y' is a sequence which hybridizes to Y;
S' is a sequence which hybridizes to S;
wherein Y comprises or consists of a sequence $P_Y$ which is identical to priming sequence P, optionally, wherein sequence S and sequence S' form a duplex structure which is stable at a temperature between about 20° C. and about 95° C. or between about 60° C. and about 75° C.

3. The device of claim 1 or 2:
(1) wherein P is about 6 bases to about 30 bases in length,
(2) wherein Y further comprises a tag sequence T which is different from the sequence $P_Y$ and the tag sequence T is located 3' to sequence $P_Y$ and 5' to primer sequence P, optionally, wherein sequence T is about 15 bases to about 50 bases in length;
(3) comprising a 3' blocking group F which blocks extension of a sequence of the device, wherein F is located 3' to P, optionally, wherein F is an amino group, a phosphate, or a dideoxynucleotide;
(4) comprising one or more modified internucleotide linkages which are not cleavable by an enzyme, optionally, wherein the one or more modified internucleotide linkages are located 5' to product sequence Y; and/or
(5) comprising a sequence X located 5' to Y' and comprising a nucleotide sequence of about 1 base to about 25 bases in length, wherein X (i) does not hybridize to P, (ii) hybridizes to at least a portion of P, or (iii) hybridizes to at least a portion of P and to at least a portion of Y, optionally, wherein X hybridizes to only a portion of P or hybridizes to only a portion of P and to only a portion of Y or X does not hybridize to P and comprises a nucleotide sequence of about 1 to about 10 bases in length.

4. The device of claim 1 or claim 2, wherein R is (i) an abasic site, (ii) a modified base, (iii) a base which is absent from product sequence Y or is present in a reaction mixture at a limiting concentration, or (iv) a spacer.

5. The device of claim 4,
(1) wherein the modified base comprises a chemical moiety which sterically hinders a polymerase activity to or beyond R;
(2) wherein the modified base is a base which is cross-linked to another base of the oligonucleotide;
(3) wherein the modified base is cross-linked to a base of S';
(4) wherein the abasic site does not specifically bind to a base of sequence S' or sequence Y'; and/or
(5) wherein the spacer is a hexamethylene glycol spacer, a hexylene glycol spacer, or a 2-deoxyribose spacer.

6. The device of claim 1 or claim 2, wherein the sequence of S comprises a GC content between about 0% to about 100%, between about 70% and about 100% or between about 80% and about 100%.

7. A composition comprising at least two devices according to claim 1 or claim 2, optionally, (i) wherein at least two devices in the composition comprise a first device comprising a product sequence $Y_1$ and a second device comprising a product sequence $Y_2$, wherein $Y_1$ is different from $Y_2$, or (ii) wherein the composition comprises a plurality of devices of claim 1 or claim 2, wherein the plurality comprises at least three subsets of devices, wherein each device of a subset comprises a product sequence Y which is (i) the same as the sequence Y of another device of the same subset and (ii) different from the sequence Y of a device of another subset of the plurality.

8. A composition comprising at least two devices, wherein each device (i) is a polynucleotide comprising Structure 1:

Structure 1:

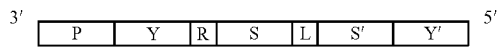

wherein:
P is a primer sequence through which at least the 3' end of the target molecule hybridizes to the device;
Y is product sequence;
R is replication blocking group;
S is a stem sequence;
L is a loop region;
S' is a sequence which hybridizes to S;
Y' is a sequence which hybridizes to Y; and
wherein each of S and S' is optionally present in the device, wherein the presence of S' is dependent on the presence of S in the device,
wherein Y, R, S, L, S', and Y' form a hairpin structure,
or (ii) comprises a first polynucleotide of Structure 2:

Structure 2

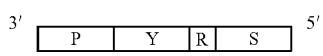

and a second polynucleotide of Structure 3:

Structure 3

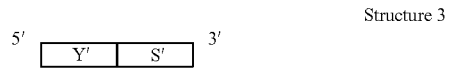

wherein:
P is a primer sequence through which at least the 3' end of the target molecule hybridizes to the device;
Y is product sequence;
R is replication blocking group;
S is a stem sequence;
Y' is a sequence which hybridizes to Y;
S' is a sequence which hybridizes to S;
wherein each device of the composition comprises a product sequence Y consisting of an additional sequence A which is not identical to priming sequence P,
wherein the composition comprises a first device comprising a primer sequence $P_1$ and a product sequence $Y_1$ and a second device comprising a primer sequence $P_2$ and a product sequence $Y_2$, wherein $P_1$ is different from $P_2$ and $Y_1$ is different from $Y_2$, wherein the complement of $Y_1$ is complementary to primer sequence $P_2$;
optionally, wherein the composition comprises a plurality of devices, wherein the plurality comprises at least three subsets of devices, wherein each device of each subset comprises a product sequence Y which is (i) the same as the sequence Y of another device of the same subset and (ii) different from the sequence Y of a device of another subset of the plurality.

9. A kit comprising a device of claim 1 or claim 2, or a composition of claim 8, and instructions for using the device or composition in a reaction which extends a single stranded primer.

10. The composition of claim 8, further comprising a polymerase and free nucleotides, wherein the polymerase is selected from the group consisting of a strand displacement polymerase, a strand displacement polymerase which operates under substantially isothermal conditions, a DNA polymerase, an RNA polymerase, a 5' exonuclease-minus polymerase, a polymerase that dissociates from the device when in contact with replication blocking group R, a polymerase that dissociates from the device under substantially isothermal conditions, and at least two polymerases, wherein at least one polymerase is a proofreading polymerase, optionally, wherein the proofreading polymerase removes bases from the single stranded target molecule that are added via one or more non-template addition reactions.

11. A method of extending a single stranded target molecule, comprising contacting the single stranded target molecule with an extension reaction mixture comprising (i) a device of claim 1 or claim 2 or a composition of claim 8, (ii) a polymerase, and (iii) free nucleotides, whereupon an extension reaction product is generated, wherein the extension reaction product comprises the single stranded target molecule with a 3' sequence complementary to product sequence Y of the device.

12. A method of extending a single stranded target molecule, comprising contacting the single stranded target molecule with an extension reaction mixture comprising (i) a composition of claim 8, (ii) a polymerase, and (iii) free nucleotides, whereupon an extension reaction product is generated, wherein the extension reaction product comprises the single stranded target molecule with a 3' sequence complementary to product sequence Y of the device,
wherein the extension reaction product generated from a first extension reaction using the first device is further extended by a second extension reaction using the second device, wherein the extension reaction product includes a 3' terminal sequence 5'(cP1-cY1-cY2)3', wherein cP1 is a sequence which is complementary to P1, cY1 is a sequence which is complementary to Y1 and cY2 is a sequence which is complementary to Y2, or wherein the extension reaction mixture comprises a composition of claim 8, wherein the extension reaction product generated from a first extension reaction using a device of a first subset is further extended by a second extension reaction using a device of a second subset, wherein the extension reaction product generated from a second extension reaction using a device from a third subset, optionally, wherein (i) the extension reaction mixture comprises n subsets of devices, (ii) the method comprises n extension reactions in which a sequence complementary to additional sequence A of the device used in the extension reaction is consecutively added to the 3' end of the target molecule, and (iii) the extension reaction product generated from the $n^{th}$ extension reaction comprises n different added sequences, each added sequence is complementary to additional sequence A of a device of each subset.

13. A method of extending a single stranded target molecule, comprising contacting the single stranded target molecule with an extension reaction mixture comprising (i) a device of claim 1 or claim 2, (ii) a polymerase, and (iii) free nucleotides, whereupon an extension reaction product is generated, wherein the extension reaction product comprises the single stranded target molecule with a 3' sequence complementary to product sequence Y of the device, wherein product sequence Y of the device consists of a sequence $P_Y$ which is identical to primer sequence P of the device, wherein at least a portion of the target molecule sequence is complementary to the primer sequence P, and wherein the extension reaction product has a 3' terminal sequence that is complementary to the primer sequence P, and optionally further comprising n extension reactions and the extension reaction product generated from the $n^{th}$ extension reaction comprises (n+1) cP sequences, wherein cP is a sequence complementary to the primer sequence P.

14. A method of extending a single stranded target molecule, comprising contacting the single stranded target molecule with an extension reaction mixture comprising (i) a device of claim 1 or claim 2:
(1) wherein P is about 6 bases to about 30 bases in length;
(2) wherein Y further comprises a tag sequence T which is different from the sequence PY and the tag sequence T is located 3' to sequence PY and 5' to primer sequence P, optionally, wherein sequence T is about 15 bases to about 50 bases in length;
(3) comprising a 3' blocking group F which blocks extension of a sequence of the device, wherein F is located 3' to P, optionally, wherein F is an amino group, a phosphate, or a dideoxynucleotide;
(4) comprising one or more modified internucleotide linkages which are not cleavable by an enzyme, optionally, wherein the one or more modified internucleotide linkages are located 5' to product sequence Y; and/or
(5) comprising a sequence X located 5' to Y' and comprising a nucleotide sequence of about 1 base to about 25 bases in length, wherein X (i) does not hybridize to P, (ii) hybridizes to at least a portion of P, or (iii) hybridizes to at least a portion of P and to at least a portion of Y, optionally, wherein X hybridizes to only a portion of P or hybridizes to only a portion of P and to only a portion of Y or X does not hybridize to P and comprises a nucleotide sequence of about 1 to about 10 bases in length;
(ii) a polymerase, and (iii) free nucleotides, whereupon an extension reaction product is generated, wherein the extension reaction product comprises the single stranded target molecule with a 3' sequence complementary to product sequence Y of the device, wherein product sequence Y of the device comprises sequence $P_Y$ which is identical to primer sequence P of the device and further comprises a tag sequence T which is different from the sequence of sequence $P_Y$ and sequence T is located 3' to $P_Y$, and optionally further comprising n extension reactions and the extension reaction product generated from the $n^{th}$ extension reaction comprises cP followed by n number of (cT-cP) sequences, wherein cP is a sequence complementary to the primer sequence P and cT-cP is a sequence complementary to the tag sequence T followed by a sequence complementary to the primer P, or wherein the extension reaction mixture comprises a plurality of devices of claim 1 or claim 2, wherein the plurality comprises at least three subsets of devices, wherein each device of a subset comprises a sequence Y sequence which is (i) the same as sequence Y of another device of the same subset and (ii) different from sequence Y of a device of another subset of the plurality, wherein the extension product has a 3' terminus which comprises a sequence which is complementary to each of sequence Y of the plurality.

15. The method of claim 11, wherein the method is carried out under substantially isothermal conditions, optionally within a range of about 20° C. to about 95° C.

16. The method of claim 11, wherein the method comprises one or more steps carried out at a first temperature and one or more steps carried out at a second temperature, wherein the second temperature is at least or about 25° C. greater than the first temperature, optionally wherein the first temperature is within a range of about 60° C. to about 75° C. and the second temperature is within a range of about 85° C. to about 100° C., and/or comprising a dissociation step in which the polymerase dissociates from the device at the second temperature.

* * * * *